US010786184B2

United States Patent
Bochner et al.

(10) Patent No.: US 10,786,184 B2
(45) Date of Patent: Sep. 29, 2020

(54) METHOD FOR DETERMINING HEARING THRESHOLDS IN THE ABSENCE OF PURE-TONE TESTING

(71) Applicants: Joseph H. Bochner, Victor, NY (US); Wayne M. Garrison, Baltimore, MD (US)

(72) Inventors: Joseph H. Bochner, Victor, NY (US); Wayne M. Garrison, Baltimore, MD (US)

(73) Assignee: Rochester Institute of Technology, Rochester, NY (US)

( * ) Notice: Subject to any disclaimer, the term of this patent is extended or adjusted under 35 U.S.C. 154(b) by 413 days.

(21) Appl. No.: 15/801,765

(22) Filed: Nov. 2, 2017

(65) Prior Publication Data
US 2018/0132765 A1 May 17, 2018

Related U.S. Application Data

(62) Division of application No. 14/736,452, filed on Jun. 11, 2015, now Pat. No. 9,833,174.
(Continued)

(51) Int. Cl.
*A61B 5/12* (2006.01)
*G10L 25/66* (2013.01)
*G10L 15/00* (2013.01)

(52) U.S. Cl.
CPC .............. *A61B 5/123* (2013.01); *G10L 25/66* (2013.01); *G10L 15/00* (2013.01)

(58) Field of Classification Search
None
See application file for complete search history.

(56) References Cited

U.S. PATENT DOCUMENTS 7,206,416 B2    4/2007   Krause et al.
9,313,585 B2 *   4/2016   Lunner ................ H04R 25/505
(Continued)

FOREIGN PATENT DOCUMENTS

WO    WO2002093980 A2    11/2002
WO    WO2005018275 A2    2/2005
(Continued)

OTHER PUBLICATIONS

Doherty, K., Bochner, J., Garrison, W., Richards, G., Holstad, K. & Sims, D. (2012). An Adaptive Test for the Clinical Measurement of Speech Recognition. Poster presented at Audiology NOW!, Boston, MA, Mar. 30, 2012.
(Continued)

*Primary Examiner* — Sean P Dougherty
*Assistant Examiner* — Benjamin S Melhus
(74) *Attorney, Agent, or Firm* — Bond, Schoeneck & King, PLLC; Jospeh Noto

(57) ABSTRACT

A method for determining hearing thresholds in the absence of pure-tone testing includes an adaptive speech recognition test which includes a calibrated item pool, each item having a difficulty value ($d_i$) and associated standard error ($s_e$). Test items are administered to a group of individuals having mild to moderately severe hearing loss to obtain responses. The responses are subjected to multiple regression statistical methods to develop an equation for converting an individual's test score to hearing threshold values at several frequencies. The adaptive speech recognition test can be administered to an individual and their score can be converted into hearing thresholds at each of the several frequencies by use of the equation.

15 Claims, 2 Drawing Sheets

Related U.S. Application Data

(60) Provisional application No. 62/011,396, filed on Jun. 12, 2014.

(56) References Cited

U.S. PATENT DOCUMENTS

| | | | |
|---|---|---|---|
| 2001/0046658 A1* | 11/2001 | Wasowicz | G09B 5/065 434/167 |
| 2005/0027537 A1 | 2/2005 | Krause et al. | |
| 2005/0153263 A1* | 7/2005 | De Ley | G09B 5/00 434/169 |
| 2007/0286350 A1 | 12/2007 | Krause et al. | |
| 2010/0232601 A1 | 9/2010 | Itoh et al. | |
| 2010/0232613 A1* | 9/2010 | Krause | A61N 1/08 381/60 |
| 2012/0051569 A1 | 3/2012 | Blarney et al. | |
| 2013/0085411 A1* | 4/2013 | Van Tasell | A61B 5/12 600/559 |
| 2015/0118661 A1* | 4/2015 | Haruta | G06F 19/3481 434/169 |
| 2015/0245150 A1* | 8/2015 | Jepsen | H04R 25/70 381/314 |
| 2016/0262651 A1* | 9/2016 | Thai-Van | A61B 5/04009 |

FOREIGN PATENT DOCUMENTS

| | | |
|---|---|---|
| WO | WO2008025858 A2 | 3/2008 |
| WO | WO2010091480 A1 | 8/2010 |
| WO | WO2010117710 A1 | 10/2010 |
| WO | WO2012127445 A2 | 9/2012 |

OTHER PUBLICATIONS

Bochner, J., Garrison, W., Sussman, J. and Burkard, R. (2003). Development of materials for the clinical assessment of speech recognition: The Speech Sound Pattern Discrimination Test. Journal of Speech, Language and Hearing Research. 46, 889-900.

Bochner, J., Garrison W., Palmer, L., MacKenzie, D., and Braveman, A. (1997). A computerized adaptive testing system for speech discrimination measurement: The Speech Sound Pattern Discrimination Test (SSPDT). Journal of the Acoustical Society of America, 101(4), 2289-2298.

American Speech-Language-Hearing Association 1997. Guidelines for audiologic screening. ASHA.

Foulad, A., Boi, P. & Djalilian, H. 2013. Automated audiometry using Apple iOS-based application technology. Otolaryngol Head Neck Surg, 700-706.

Handzel, O., Ben-Ari, O., Damian, D., Priel, M. M., Cohen, J. et al. 2013. Smartphone-based hearing test as an aid in the initial evaluation of unilateral sudden sensorineural hearing loss. Audiol Neurotol, 18, 201-207.

Kam, A. C. S., Gao, H., Li, L. K. H., Zhao, H., Qiu, S. et al. 2013. Automated hearing screening for children: a pilot study in China. Int J Audiol, 52, 855-860.

Kam, A. C. S., Sung, J. K. K., Lee, T., Wong, T. K. C., & van Hasselt, A. 2012. Clinical evaluation of a computerized self-administered hearing test. Int J Audiol, 51, 606-610.

Khoza-Shangase, K. & Kassner, L 2013. Automated screening audiometry in the digital age: exploring UHEAR and its use in a resource-stricken developing country. Int J Technol Assess Health Care, 29, 42-47.

Leensen, M.C. de Laat, J.A. & Dreschler, W.A. 2011. Speech-in-noise screening tests by internet, part 1: test evaluation for noise-induced hearing loss identification. Int J Audiol, 50, 823-834.

McPherson, B., Law, M. M. & Wong, M.S. 2010. Hearing screening for school children: comparison of low-cost, computer-based and conventional audiometry. Child Care Health Dev, 36, 323-331.

Molander, R, Nordqvist, P., Oberg, M., Lunner, T., Lyxell, B. et al. 2013. Internet-based hearing screening using speech-in-noise: validation and comparisons of self-reported hearing problems, quality of life and phonological representation. BMJ Open, 3, e003223.

Paglialonga, A., Grandori, F & Tognola, G. 2013. Using the speech understanding in noise test for adult hearing screening. Amer J Audiol, 1-4.

Paglialonga A. Tognola, G. & Grandori, F. 2011. SUN-test (Speech Understanding in Noise): a method for hearing disability screening. Audiol Res, 1:e13, 49-54.

Smits, C, Kapteyn, T. S. & Houtgast, T. 2004. Development and validation of an automatic speech-in-noise screening test by telephone. Int J Audiol, 43, 15-28.

Smits, C., Merkus, P. & Houtgast, T. 2006. How we do it: the Dutch functional hearing-screening tests by telephone and internet. Clin Otolaryn, 31, 436-440.

Stenfelt, S., Janssen, T., Schirkonyer, V. & Grandori, F. 2011. E-Health technologies for adult hearing screening. Audio Res, 1(e14), 55-57.

Swanepoel, D. W., Myburgh, C. M., Howe, D. M., Mahomed, F. & Eikelboon, R. H. 2014. Smartphone hearing screening with integrated quality control and data management. Int J Audiol, 53(12), 841-849.

Szudek, J., Ostevik, A., Dziegielewski, P., Robinson-Anagor, J., Gomaa, N. et al. 2012. Can u hear me? Validation of an iPod-based hearing loss screening test. J Otolaryngol Head Neck Surg, 41, S78-S84.

Ventry, I. M. & Weinstein, B.E. 1982. The hearing handicap inventory for the elderly: a new tool. Ear Hear, 3, 128-134.

Vlaming, M. S. M. G., Kollmeier, B., Dreschler, W. A., Martin, R., Wouters, J. et al. 2011. HearCom: hearing in the commmunication society. Acta Acoustica, 97, 175-192.

Watson, C. S. Kidd, G. R. Miller, J. D. Smits, C. & Humes, L. E. 2012 Telephone screening tests for functionally Impaired hearing: Current use in seven countries and development of a US version. J Am Acad Audiol, 23, 757-767.

Williams-Sanchez, V., McArdle, R. A., Wilson, R. H., Kidd, G. R., Watson, C. S. et al. 2014. Validation of a screening test of auditory function using the telephone. J Am Acad Audiol, 25(10), 937-951.

Zokoll, M. A., Wagener, K. C., Brand, T., Buschermohle, M. & Kollmeier, B. 2012. Internationally comparable screening tests for listening in noise in several European languages: The German Digit Triplet Test as an optimization prototype. Int J Audiol, 51,697-707.

Coren, Stanley, Predicting Speech Recognition Thresholds From Pure Tone Hearing Thresholds, Nov. 1994, Perceptual and Motor Skills, vol. 79, p. 1003-1008 | DOI: 10.2466/pms.1994.79.2.1003.

\* cited by examiner

Observed vs. predicted hearing thresholds for four subgroups of respondents.

METHOD FOR DETERMINING HEARING THRESHOLDS IN THE ABSENCE OF PURE-TONE TESTING

CROSS REFERENCE

This application is a divisional of U.S. Non-Provisional Application 14/736,452 filed Jun. 11, 2015, which claimed benefit of U.S. Provisional Application No. 62/011396 filed Jun. 12, 2014, the subject matters of which are incorporated herein by reference in their entireties.

FIELD

This invention provides a method for determining hearing thresholds in the absence of pure-tone testing and, in particular, a method for determining hearing thresholds through speech recognition of an individual in the absence of pure-tone testing.

BACKGROUND

To date, speech recognition scores have not been used to predict hearing thresholds. Hearing thresholds are not highly correlated with scores on conventional measures of speech recognition and, as such, it is counterintuitive that scores on any measure of speech recognition could be used to predict hearing thresholds.

The degree of an individual's hearing loss generally is quantified in terms of the magnitude or level of a sound needed for him/her to detect it. The smallest intensity of a sound needed by a person to detect its presence is referred to as his/her threshold for that sound. In practice, hearing threshold is defined as the lowest intensity at which an individual responds to a sound on approximately half of the occasions on which it is presented. Typically, the sounds used to test an individual's hearing are pure tones presented at different frequencies (i.e., octave intervals from 0.25 kHz to 8 kHz). Standard audiometric evaluations include the determination of pure-tone thresholds. Providing clinicians with estimates of clients' hearing thresholds prior to the audiometric evaluation could enhance efficiency in clinical practice in the same way that ophthalmologists enhance efficiency by having a technician administer an eye test for refraction prior to the patient seeing the doctor.

In clinical practice, hearing thresholds are determined via a standard testing procedure administered by an audiologist using specialized equipment (a properly calibrated clinical audiometer) in a specialized environment (a sound-treated booth) and, as such, cannot be determined over the internet. Hearing thresholds indicate the severity and configuration of hearing loss and serve as the input for programming hearing aids. They also can be used to determine whether or not a personal sound amplification product (PSAP) would be an appropriate option for individual consumers. Currently, people wishing to purchase a PSAP often have no way of knowing if it would be appropriate for them, so having information concerning their hearing thresholds would empower consumers to make better health care decisions. In addition, individuals wishing to purchase a programmable hearing aid over the internet must see a hearing health care provider to obtain their hearing thresholds. This represents an additional cost to the consumer. Hearing aid sales, unlike the sale of PSAPs, are regulated by the Food and Drug Administration, as well as state authorities. As such, government regulations currently require consumers to visit a licensed hearing health care provider in order to obtain their hearing thresholds for the purpose of programming hearing aids. Therefore, in principle, enabling hearing thresholds to be determined using a self-administered test delivered over the internet has the potential to facilitate direct sales of PSAPs and hearing aids to consumers, significantly reducing cost and increasing accessibility for millions of individuals.

Hearing aids are beginning to be sold directly to consumers over the internet at deep discounts from the normal retail cost. By selling hearing aids at deeply discounted prices, distributors are likely to cut into revenue for audiologists working within the current business model in which they serve as middlemen for dispensing hearing aids to consumers. Similarly, PSAPs cost considerably less than hearing aids and also are available over the internet and at some pharmacies and other retailers. The sale of these devices also is likely to cut into revenue for audiologists. The problem with the current business model in hearing health care is that it is not sustainable because the middleman's mark-up and services more than double the consumer's cost. Therefore, it is likely that hearing aids and PSAPs will continue to be sold directly to consumers over the internet, and alternative means of obtaining hearing thresholds will be needed to maximize their sales and accessibility to members of the general public, especially to first-time users of amplification and individuals who are highly cost-conscious.

SUMMARY

In accordance with one aspect of the present invention, a method is provided for determining hearing thresholds in the absence of pure-tone testing including developing a speech recognition test including a plurality of items, each item containing a plurality of utterances; administering items from the plurality of items of the speech recognition test to a first group of individuals having mild to moderately severe hearing loss to obtain a response to the items; subjecting the responses to a scaling analysis to assign a difficulty value ($d_i$) and associated standard error ($s_e$) to the items to create an adaptive speech recognition test including a calibrated item pool; administering the adaptive speech recognition test including items from the calibrated item pool to a second group of individuals having mild to moderately severe hearing loss to obtain a response to the calibrated items; calculating a test score for each individual based upon the responses to the calibrated items; applying multiple regression statistical methods to the test scores of the second group together with variables including an individual's age and perception of hearing handicap to develop an equation for converting an individual's adaptive speech recognition test score to hearing threshold values at several frequencies; administering the developed adaptive speech recognition test to an individual; and converting the test score from the individual by use of the equation into at least one of the hearing threshold values.

In accordance with the present invention, a method for determining hearing thresholds in the absence of pure-tone testing is provided, including:

administering an adaptive speech recognition test to an individual and obtaining a test score;

calculating a hearing threshold designated as $y_j$ for the individual at least at one of the following frequencies, wherein j=0.5, 1, 2, 4, and 8 kHz using the formula $$y_j = b_{j0} + b_{j1}x_1 + b_{j2}x_2 + b_{j3}x_3$$

wherein the value for $x_1$ expressed on a 0 to 100 scale is the test score obtained in the administered adaptive speech recognition test, the value for $x_2$ is the chronological age of the individual expressed in years, and the value for $x_3$ is the self-report of perceived hearing impairment of 1 for yes and 0 for no, wherein at j=0.5 kHz the $b_{j0}$, $b_{j1}$, $b_{j2}$, and $b_{j3}$ constants are 103.69, −1.23, −0.21, and 7.55, respectively;

at j=1 kHz the $b_{j0}$, $b_{j1}$, $b_{j2}$, and $b_{j3}$ constants are 133.27, −1.59, −0.30, and 9.40, respectively;

at j=2 kHz the $b_{j0}$, $b_{j1}$, $b_{j2}$, and $b_{j3}$ constants are 154.00, −1.92, −0.17, and 7.51, respectively;

at j=4 kHz the $b_{j0}$, $b_{j1}$, $b_{j2}$, and $b_{j3}$ constants are 144.57, −1.84, 0.06, and 11.10, respectively; and at j=8 kHz the $b_{j0}$, $b_{j1}$, $b_{j2}$, and $b_{j3}$ constants are 122.91, −1.67, 0.38, and 13.57, respectively.

These and other aspects of the present invention will become apparent upon a review of the following detailed description and the claims appended thereto.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
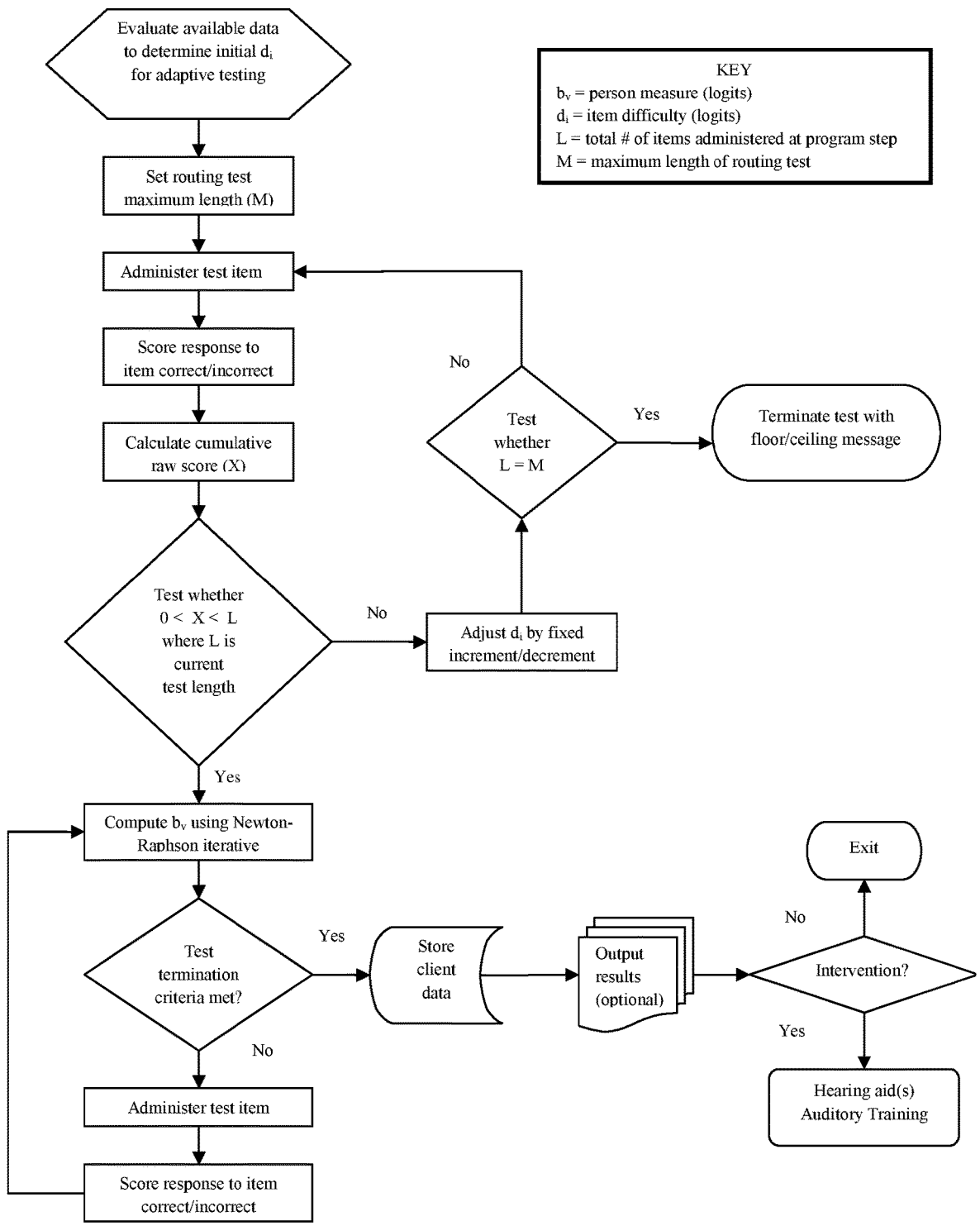
FIG. 1 depicts a flowchart illustrating the operation of the NSRT® adaptive testing system.

This invention provides a method for determining hearing thresholds of an individual in the absence of pure-tone testing. An embodiment of the method includes an adaptive speech recognition test. The adaptive speech recognition test can be administered to an individual to determine hearing thresholds of the individual. A suitable adaptive speech recognition test includes a plurality of items. In an embodiment, each item can include two trials and each trial can include two spoken utterances, e.g., a standard utterance followed by a comparison utterance. Other numbers of trials and utterances are suitable for use in the method. The comparison utterance can be the same or different from the standard utterance in each trial. The plurality of items may be referred to herein as the pool of items or item pool. A suitable adaptive speech recognition test can be developed by administering items from the item pool to a first group of individuals having mild to moderately severe hearing loss to obtain their responses. In an embodiment, each one of the items in the item pool is administered to each member of the first group of individuals to obtain their responses to each item. An item is scored correct if and only if the response to both trials is correct. The responses to the items from the first group of individuals are subjected to a scaling analysis to assign a difficulty value ($d_i$) and associated standard error ($s_e$) to each item, thereby creating a calibrated item pool. The calibrated item pool can be used for adaptive speech recognition testing of a second group of individuals to develop an equation for converting adaptive speech recognition test performance into hearing thresholds. The second group of individuals can be the same or different than the first group of individuals. Items from the calibrated item pool are administered to the second group of individuals having mild to moderately severe hearing loss to obtain their responses. In an embodiment, a subset of the items in the calibrated item pool is administered using the adaptive test to each member of the second group of individuals to obtain their responses to each item. An item is scored correct if and only if the response to both trials is correct. The responses to each item are used to calculate a test score for each individual. Multiple regression statistical methods are applied to the test scores of the second group together with other variables, such as an individual's age and perception of hearing handicap to develop an equation for converting an individual's test score to hearing threshold values at several frequencies. The adaptive speech recognition test can be administered to a single individual to obtain a test score. The test score can be converted into hearing thresholds of the individual at each of the several frequencies using the equation.

The adaptive speech recognition test is a diagnostic tool which produces data that can be used for predicting hearing thresholds, screening for hearing loss and other purposes for the individual tested (e.g., determining whether a personal sound amplification product (PSAP) might be an appropriate option for a consumer and saving clinicians time by guiding them to clients' hearing thresholds). The adaptive speech recognition test can be delivered by methods known in the art, such as via a computer-interactive assessment system. The test can be administered, for example, by a software application to efficiently provide meaningful information about the perceptual capabilities of listeners across a wide range of hearing thresholds, including mild to profound hearing losses.

An embodiment for developing suitable items for use in the present method includes stimulus materials composed of utterances which include linguistic contrasts (primarily minimal pairs). Preferably, naturalistic sentence-length utterances are used; but utterances composed of single words, phrases or more than one sentence also can be used. The linguistic contrasts contained in the utterances involve phonetic features of consonants such as place, manner, and voicing, as well as features of vowels. In addition to segmental contrasts in phonetic features of place, manner and voicing and features of vowels, the test includes items containing contrasts in sentence prosody (i.e., gross time-intensity variations in the speech waveform envelope combined with contrasts at the syllable and word levels). Preferably, the test contains linguistic contrasts distributed over four broad linguistic categories: 1) sentence prosody; 2) voicing and vowels; 3) manner of articulation; and 4) place of articulation.

Contrasts in place of articulation are manifested within voiced and voiceless stop and fricative consonants (i.e., /p-t/, /p-k/, /t-k/, /b-d/, /b-g/, /d-g/, /f-s/, /f-ʃ/, /s-ʃ/, /θ-s/, /θ-ʃ/, /θ-f/, /z-v/, /v-ð/ and /z-ð/). The location of place contrasts varies in serial position within words and within sentences (i.e., word- and sentence-initial, medial and final positions; sentence-initial position is defined herein as the first phrase in a sentence; sentence-final position is defined as the last phrase in a sentence; and sentence-medial position is defined as all other locations within the sentence). Preferably, about 35% of all contrasts occur in this category. In other embodiments, approximately 25-45% of all contrasts occur in the place category. Examples of place contrasts are included in Table 1.

Contrasts in manner of articulation are manifested within voiced and voiceless stop and fricative consonants produced at the labial and alveolar places of articulation (i.e., /t-s/, /t-ʃ/, /t-θ/, /z-d/, /f-p/, /v-b/, and/d-ð/). The location of manner contrasts varies in serial position within words and within sentences (i.e., word- and sentence-initial, medial and final positions). Preferably, about 25% of all contrasts occur in this category. In other embodiments, approximately 15-35% of all contrasts occur in the manner category. Examples of manner contrasts are included in Table 1.

Contrasts in voicing are manifested within voiced-voiceless cognates (i.e., stops and fricatives), and contrasts in vowels are manifested across the features of tongue height and tongue advancement, as well as tense-lax vowel pairs. Again, the location of these contrasts varies in serial position within words and within sentences (i.e., word- and sentence-initial, medial and final positions). Preferably, about 20% of all contrasts occur in this category. In other embodiments, approximately 10-30% of all contrasts occur in the voicing and vowels category. Examples of voicing and vowel contrasts are included in Table 1.

Contrasts in sentence prosody (i.e., gross time-intensity variations in the speech waveform envelope combined with contrasts at the syllable and word levels) are manifested within and between phonological phrases, and their location varies within sentences. Preferably, about 20% of all contrasts occur in this category. In other embodiments, approximately 10-30% of all contrasts occur in this category. Examples of contrasts in sentence prosody are included in Table 1.

Preferably, about 30% of the contrasts located within words occur in word-initial position; about 30% occur in word-final position; and about 40% occur in word-medial position. In other embodiments, approximately 20-40% of the contrasts located within words occur in word-initial position; about 20-40% occur in word-final position; and about 30-50% occur in word-medial position. With regard to the location of contrasts within sentences, preferably about 20% of contrasts occur in sentence-initial position; about 30% occur in sentence-final position; and about 50% occur in sentence-medial position. In other embodiments, approximately 10-30% of contrasts occur in sentence-initial position; about 20-40% occur in sentence-final position; and about 40-60% occur in sentence-medial position.

TABLE 1

Place Contrasts
    1. Free books are available. (standard)
        a. Free books are available. (comparison)
        b. Three books are available. (comparison)
    2. The soldiers spared the children. (standard)
        a. The soldiers scared the children. (comparison)
        b. The soldiers scared the children. (comparison)
    3. The committee is working to revise the proposal. (standard)
        a. The committee is working to revive the proposal. (comparison)
        b. The committee is working to revive the proposal. (comparison)
Manner Contrasts
    4. Many tourists visit the old fort every summer. (standard)
        a. Many tourists visit the old port every summer. (comparison)
        b. Many tourists visit the old port every summer. (comparison)
    5. He's an awful cheap executive. (standard)
        a. He's an awful chief executive. (comparison)
        b. He's an awful cheap executive. (comparison)
    6. Don't pass the bread! (standard)
        a. Don't pass the bread! (comparison)
        b. Don't pat the bread! (comparison)
Voicing and Vowel Contrasts
    7. The workers painted a wide stripe on the street. (standard)
        a. The workers painted a white stripe on the street. (comparison)
        b. The workers painted a white stripe on the street. (comparison)
    8. Tyson beat his opponent. (standard)
        a. Tyson bit his opponent. (comparison)
        b. Tyson bit his opponent. (comparison)

TABLE 1-continued

Sentence Prosody Contrasts
    9. The schools closed yesterday. (standard)
        a. The schools closed early. (comparison)
        b. The schools closed yesterday. (comparison)
    10. The accident was caused by poor visibility. (standard)
        a. The accident was caused by poor visibility. (comparison)
        b. The serious accident was caused by poor visibility. (comparison)

A fifth category of items representing repetitions of the standard sentence also is included in the item pool. This category does not contain any contrastive linguistic elements. Both comparison sentences are repetitions of the standard sentence and, as such, the correct response to each trial for items in this category is 'Same.' Preferably, about 10% of the item pool is composed of items in this category.

Preferably, the utterances are produced by an adult male voice speaking in a General/Standard American English dialect. Alternately, an adult female voice may be used separately or in combination with a male voice. The utterances also may be produced in other social or regional dialects of English either separately or in combination with the standard dialect.

In accordance with an embodiment, the utterances are recorded, preferably digitally, and edited to develop a set of audio files. Each audio file is composed of one utterance. The utterances (audio files) are used to construct the test items. The stimuli are digitally recorded at a sampling rate of at least 10 kHz and edited using signal processing software. Preferably, a sampling rate of 11.025 kHz or 22.050 kHz is used. Multiple renditions/tokens of each utterance are recorded, and a good quality, representative token is selected for inclusion in the test. The level of each utterance is adjusted to equalize the overall RMS voltage across stimuli in order to present each stimulus at an approximately equivalent overall level. Although the overall level of each sentence is equivalent, RMS voltage within sentences varies with oscillations in the amplitude of the waveform.

Each of the recorded materials (test items) is administered to a sample of individuals having mild to moderately severe hearing loss. Each test item is presented to each respondent using a paired comparison discrimination task. For example, a common-item test composed of at least 250 items may be administered to a sample of at least 30 respondents. Preferably, a common-item test composed of approximately at least 600 items is administered to a sample of at least 100 respondents. However, other size groups and number of test items are suitable for use in the present method.

Although it is possible to design and administer computerized adaptive tests without item response theory (IRT), IRT-based systems have advantages over those which are not IRT-based and thus are preferred. Chief among these advantages is placement of the item difficulty ($d_i$) and person ability ($b_v$) estimates on the same numerical scale in IRT, facilitating the selection of items of appropriate difficulty for an individual. IRT scoring procedures also make it possible to estimate a respondent's ability level and the associated standard error or precision immediately following the administration of each test item, the former statistic aiding in item selection, the latter being useful for terminating a testing session.

IRT models are mathematical abstractions based upon suppositions about what happens when an examinee responds to a test item. The simplest of the IRT models, also the basis of the current test method, is the Rasch (1960) one-parameter logistic model. Item difficulty is an intrinsic parameter of item response theory models, with variations in item difficulty being necessary for the creation of item pools used in adaptive testing. The Rasch model differs significantly from more complicated models in that it is not intended to fit data. Rather, the Rasch model is a definition of measurement. When data are found to fit the model, the measurement of persons and the assignment of difficulty values to items (i.e., calibration of items) enable the placement of persons and items on a common scale which functions according to the rules of arithmetic. This scale uses a logarithmic unit of measurement known as the logit. The logit metric applies to both items and test takers. That is, the logit is a measure of both item difficulty and person ability.

Data obtained from administration of the common-item tests administered to respondents are subjected to Rasch scaling analysis to develop the calibrated item pool. This analysis assigns a difficulty value ($d_i$) and associated standard error ($s_e$) to each item of the test. The difficulty value and standard error associated with each item enable the items to be scaled along a continuum of difficulty, providing the basis for the "up-down" psychophysical method of item selection used in adaptive testing.

The Rasch model for person measurement conceptualizes success or failure on any test item as a function of the difference between an examinee's position on an ability continuum and the difficulty of items scaled along the same continuum. The way that this difference governs the outcome of the person-item interaction is then modeled probabilistically.

In its simplest form, the Rasch model can be presented as follows:

$$\text{Probability } \{x_{vt}=1\}=\exp(\beta_v-\delta_t)/[1+\exp(\beta_v-\delta_t)]$$

where $x_{vt}=1$ if person v responds correctly to item ι;
$\beta_v$ =a parameter describing the ability of person v; and
$\delta_t$=a parameter describing the difficulty of item ι.

In the above formulation, β and δ can assume all real values and measure ability and difficulty respectively on the logit scale which they share. The sign of the difference between the two parameters in any particular instance indicates the probable outcome of the person-item interaction. If $\beta_v > \delta_t$ the most probable outcome is a correct response to a test item. If $\beta_v < \delta_t$ then the most probable outcome is an incorrect response.

The logistical distribution is one of two statistical distributions which have been used to model the probabilistic aspect of testing outcomes in the field of psychometrics, as well as in many other scientific and biometric applications (e.g., growth and mortality rates). The Rasch model is based upon the logistic distribution. The $\beta_v$ and $\delta_t$ that appear in the formulation above represent parameters. In practice, these parameters are estimated from observed data. The statistic estimating $\beta_v$ is $b_v$, while the statistic estimating $\delta_t$ is $d_i$.

From the foregoing discussion, the probability associated with a successful outcome on any particular person-item interaction is determined. The probability is an exponential function of the difference between $b_v$ and $d_i$. The $b_v$ estimate is obtained from an individual's testing experience. The $d_i$ values will have been obtained from previous test results. There is one $b_v$ value for each person tested, and one $d_i$ value for each item that exists within an item pool. When a respondent completes a test session, their score provides an estimate of their level of ability based upon the difficulty values of the items presented during the test session.

The responses of persons to the individual items constitute the raw data from which the item calibrations ($d_i$) and person measures ($b_v$) are obtained. In the usual scaling analysis, raw data are organized in matrix form. Persons appear as rows, items appear as columns. The data entries are 1's and 0's, where '1' represents a correct response of an individual to an item, '0' represents an incorrect response. Person scores are initially obtained by summing the 1's and 0's across items for each person tested. Item scores are initially obtained by summing the 1's and 0's across persons for each item in the test. These marginal sums are sufficient for estimating the $d_i$ and $b_v$ statistics. Preferably, a calibrated item pool composed of approximately 600 items is established with associated $d_i$ values.

Other data are obtained during the above testing to develop the equation for converting test performance into hearing thresholds. These data include, but are not limited to, respondents' age, self-perception of hearing handicap, speech recognition threshold and pure tone thresholds across the octave frequencies 0.25 through 8 kHz. Additional data include results from administrations of speech recognition tests such as scores on the CID W-22 word recognition test and the QuickSIN test. Respondents' also are asked one or more questions pertaining to their hearing ability, such as whether they perceive themselves to have hearing difficulty, and they may be asked to indicate their gender.

Multiple regression statistical methods known to those of skill in the art are applied to the data set to derive the equation for converting an individual's test score(s) to hearing threshold values, as well as to study the empirical validity of the adaptive test. The multiple regression analyses are conducted on the combined data from the respondents described above to determine how well a weighted combination of the score(s) on the adaptive speech recognition test and the other variables (i.e., age and perceived hearing ability) predict hearing thresholds across the frequency range 0.5 through 8 kHz. To reiterate, the test results are used to formulate the algorithms, and then subsequent testing of individual respondents yields data which can be transformed into hearing thresholds for each respondent. Note that, in the linear equations resulting from these analyses, the test score is preferably an average score from administrations of the test under quiet and degraded listening conditions, with the degraded condition preferably background noise (multi-talker babble) presented at +5 dB SNR. Furthermore, the test score is itself transformed from logits (output from the Rasch scaling analysis) to a new metric ranging from 0 to 100. Preferably, the correspondence between the logit metric and the transformed metric is perfect.

A general form of the equation used to compute hearing thresholds across the octave frequencies from 0.5 to 8 kHz is shown below. The results of these computations can then be combined to construct a pseudo audiogram for an individual based upon adaptive speech recognition test performance.

$$y_j = b_{j0} + b_{j1}x_1 + b_{j2}x_2 + b_{j3}x_3 \, j = 1\text{-}5 \{\text{frequencies}\}$$

where:
$x_1$=test measures obtained under quiet, noise or the average of both listening conditions (i.e., average of scores obtained in quiet and noise);
$x_2$=chronological age expressed in years; and
$x_3$=self-report of perceived hearing ability.

The metric for $x_1$ in the equation above ranges 0-100 and is itself a transformation of the logit metric used in Rasch scaling analysis. The data value for $x_1$ is an average of the test measures obtained in the quiet and degraded listening conditions, expressed on the 0-100 scale. The $b_j$ constants in the mathematical expression above are derived from the multiple regression analyses. There are five (j=5) sets of constants ($b_{j0}$, $b_{j1}$, $b_{j2}$, $b_{j3}$), corresponding to the five frequencies (0.5, 1, 2, 4, and 8 kHz) for which individuals' hearing thresholds are computed.

Once the algorithms are specified, having created a calibrated item pool, individuals can be tested with an adaptive version of the speech recognition test, substantially shorter than the common-item test, and the results can be used to convert test scores into hearing thresholds at each of the desired frequencies. The resultant hearing thresholds can be used to screen test takers for hearing loss and other purposes. Preferably, data should indicate that scores obtained from adaptive tests are statistically equivalent to those obtained using lengthier common-item test forms.

The test can be presented in quiet or in background noise, preferably multi-talker babble at +5 dB SNR. Alternate kinds of background/masking noise may be used and presented at a variety of signal to noise ratios. Similarly, other techniques for degrading the utterances also may be used (e.g., filtering). Two listening conditions have proven practical and useful, preferably quiet and multi-talker babble presented at +5 dB SNR.

In an embodiment, the adaptive speech recognition test is composed of utterances containing phonetic contrasts, primarily minimal pairs. The test uses a paired comparison discrimination task in which a written standard stimulus (accompanied by an optional vocal utterance of the standard stimulus) is paired with two comparison utterances. Respondents must decide if the standard and comparison stimuli in each trial are the same or different from each other. The presentation of an item begins with the presentation of a written representation of the standard stimulus on a computer monitor. Approximately 0.5-3 seconds after the written stimulus is displayed on the monitor and with it still remaining on the monitor, a spoken utterance (i.e., the first comparison utterance) is presented. Preferably, the spoken utterance is presented 1.5 seconds after the written stimulus appears on the monitor. Each respondent indicates if the comparison stimulus is the same or different from the standard stimulus. If the response is correct, then a second comparison stimulus is presented while the printed version of the standard stimulus remains displayed on the monitor. If the response is incorrect, then the next standard stimulus (i.e., the next item) is presented. An item is scored correct when the participant responds correctly to both comparison stimuli. No partial credit is awarded. Therefore, if the response to the first trial is incorrect, the item is scored incorrect, and the standard stimulus for the next item is presented. Elimination of the second trial in this situation is intended to reduce test administration time. All responses are recorded, preferably on a computer hard drive.

In an alternate embodiment of the above procedure, a spoken version of the standard stimulus is presented simultaneously with the written representation of the standard stimulus and before the presentation of the first comparison stimulus. Thereafter, the procedure is the same. That is, the written stimulus remains on the computer monitor while comparison utterances are presented and listeners enter their responses as described above. In yet another alternate embodiment of the procedure, an item may be composed of more than two trials. In still another embodiment, the respondent may be presented with two trials for each item regardless of whether or not their response to the first trial is correct.

Respondents are instructed to compare the standard and comparison stimuli and indicate if they match (i.e., if the stimuli have the same meaning). They are informed that any combination of 'Same' and 'Different' trials is possible, allowing for four potential response outcomes: S-D, D-S, D-D, and S-S. The test session begins after respondents demonstrate that they understand the task by successfully completing a set of 5-15 practice items. Sample test items are presented in Table 1 above.

Examinees indicate whether the stimuli presented in each trial are the 'same' or 'different.' This can be done in any manner, such as by pressing a button on a response box, clicking a computer mouse or pressing a touch screen.

The Rasch model is used to quantify the difficulty of test items scaled along the continuum extending from low to high degrees of speech recognition ability. The model enables the discovery of this continuum and the scaling of item difficulty. The continuum of item difficulty, in turn, provides an implicit hierarchy that enables the adaptive testing procedure to utilize an "up-down" method of item selection to array respondents on the same continuum as the items. The continuum of item difficulty generally reflects the listener's ability to perceive acoustic and phonetic properties of speech, such as phonetic features of place, manner and voicing. The pool of items in the test preferably includes at least 250 items and more preferably includes about 600 unique utterance pairs (items).

Since the test is suitable for being administered by a software application, it may be delivered over the internet and/or self-administered by test takers. Preferably, the software will be an internet-based application. Alternately, the software may be a desktop application.

The adaptive speech recognition test of the present invention differs from conventional speech recognition tests in that the testing experience is individualized and automated, with items being selected "on the fly" from a large pool by an objective "up-down" method on the basis of their information value. The "up-down" method of item selection is designed such that the items administered to each person are selected from a relatively narrow range of difficulty circumscribing their level of ability, which is itself constantly updated as items are administered during the testing process. The standard error associated with the respondent's performance is used to limit the range of difficulty from which items are selected for presentation within each test session. In limiting the range of difficulty from which items are selected, the up-down procedure greatly reduces measurement error in comparison to conventional word recognition tests. Importantly, the adaptive item selection procedure enhances measurement precision for individuals in comparison to conventional word recognition tests because of the systematic manner in which the up-down psychophysical method brackets the respondent's speech recognition ability level within progressively smaller ranges of measurement error. The standard error ($s_e$) determines the step size for the up-down procedure and can be set at values of ±1.0, ±1.5 or ±2.0 $s_e$ depending upon the psychometric properties of the item pool and the level of measurement precision desired. Preferably, a setting of ±1.5 $s_e$ is used as the default value.

Scores on the test have been shown to be highly reliable, having an internal consistency reliability of 0.98, as determined by the person separation reliability index commonly used in Rasch scaling analysis. Prespecification of the level of measurement accuracy or reliability required of respondents is built into the functionality of the adaptive testing software. In practice, there is a trade-off between the accuracy of test results and test administration time. As more test items are administered to a respondent, the accuracy (reliability) of the test score increases and so does the test administration time. Therefore, in practice, examiners can determine an appropriate balance between the accuracy of test results and test administration time.

The test can be administered in both quiet and background noise of 20-talker babble presented at +5 dB SNR. The software application enables test length, defined in terms of the maximum number of items (e.g., 10-60 items) and/or time of test duration (e.g., 3-20 minutes) to be varied. For example, elderly individuals in good physical health generally complete about 35 items within a five-minute test. Preferably, the test uses a maximum length of 40 items and a maximum duration of 5 minutes. Also, reliability values can be changed to different settings (e.g., 0.75, 0.80, 0.85 or 0.90), as can standard error of measurement (±1.0, ±1.5 or ±2.0), in an effort to achieve specific degrees of measurement precision. Preferably, the test uses 0.90 as the default setting for reliability and ±1.5 as the default setting for standard error. These values have proven practical and useful within the context of the present invention.

The test operates using a pre-calibrated item pool in a system with three main components: (1) an item selection routine; (2) an ability estimation technique; and (3) one or more rules for test termination. For example, a preferred embodiment includes approximately 600 pairs of utterances in the test item pool. An item is composed of one standard and two comparison stimuli as described above. Through differing permutations and combinations of standard/comparison stimuli within the item pool, the 600 pairs of utterances (test items) can be increased to more than 3,000 test items. Associated with each item is a $d_i$ value characterizing its location (magnitude) on the variable that is measured by the test (i.e., speech recognition ability). The $d_i$ values, expressed in logits or log units, are generally referred to as item calibrations or difficulty measures.

The test can be self-administered, for example, on a home computer, on a wireless device, in a kiosk setting or in a clinical environment. The stimuli are presented to respondents over earphones or in a sound field. The stimuli may be presented in a sound field to both ears (binaurally) or to one ear (monaurally) by isolating the non-test ear with an earplug. Alternately, the stimuli may be presented monaurally to each ear using earphones. In the preferred embodiment, a written representation of each standard stimulus appears on a computer monitor as comparison stimuli are presented acoustically. Examinees indicate whether the comparison sentences are the 'same' or 'different' via computer mouse. If no response is produced within a preset response interval, the trial is scored incorrect. Items are scored correct when both discrimination judgments (i.e., both trials) are correct. This scoring practice is designed to decrease the influence of random guessing in the ability estimation procedure. Testing can begin with several practice items.

The application can use preexisting data (e.g., respondent age and self-perception of hearing ability) to determine the difficulty ($d_i$) of the first test item to be administered to an individual. Specifically, the first item is empirically related to one or more of the following three variables: (1) prior performance on the test; (2) the respondent's age expressed in years; and (3) an indicator variable reflecting a respondent's perception of their hearing ability. Using equations derived from OLS regression techniques, these data can be used to guide the test application where testing is to begin by predicting a point on the continuum of item difficulty proximal to the respondent's level of ability. This enhances the efficiency and accuracy of measurement.

The test procedure preferably is composed of two stages. The first stage of testing, the routing test, proceeds until an individual responds correctly and incorrectly to the items presented. To illustrate, the first item administered has, for example, $d_i$=0.25 logit. If the examinee responds correctly (incorrectly), an item of greater (lesser) difficulty is administered next. The increment (decrement), here 0.50 logit, remains fixed and constant at this stage of testing. Thus, the second item to be administered will be that item in the pool having difficulty closest to +0.75 or −0.75 logit depending on the response to the previous item. The fixed increment (decrement) is continued until at least one correct and one incorrect response have been observed. The magnitude of the fixed increment may be varied depending upon the psychometric characteristics of the item pool.

It will be the case that some individuals tested may be outside the ability limits to which the test is sensitive. Thus, for individuals for whom both correct and incorrect responses have not been observed upon reaching the extremities of difficulty or easiness, testing terminates with a message indicating that these individuals have speech recognition ability levels which are indeterminate. The maximum length of the routing test (M) is set at the onset of testing (e.g., the maximum length may range from 7-14 items). Preferably, the maximum length of the routing test (M) is set to M=10 items.

When at least one correct and one incorrect response to the test items have been observed for an individual, a finite maximum likelihood estimate of ability ($b_v$), as well as its associated standard error $s_e$, can be computed. This occurs in the second stage of testing. The numerical estimation method employed here possesses the property that an individual's number right or raw score is a sufficient statistic for estimation of the ability parameter.

Using the estimate of ability $b_v$ computed in the previous programming step, test items in the pool that have not already been administered are evaluated for their potential to provide additional information about the examinee. Specifically, the next item to be administered will be that item which has $d_i$ closest to $b_v$, with the further condition that the difference between the ability estimate and the selected item's difficulty must be less than the standard error associated with the ability estimate. If these two conditions cannot be met, the testing is terminated with a message that test items of appropriate difficulty have been exhausted. After each newly selected test item is presented and the examinee's response is evaluated for correctness/incorrectness, the $b_v$ is revised, making use of the additional information. The revised $b_v$ is compared, as earlier, with the $d_i$ of items remaining in the pool that have not already been administered. In this way, test items continue to be administered to an examinee as long as the difference between the item difficulty and each newly computed $b_v$ remains within a decreasing standard error of measurement.

Testing is terminated when: (1) items remaining in the pool are of inappropriate difficulty; (2) an individual has responded to L items; (3) the testing session reaches a predetermined time limit; or (4) an individual has been tested to a predetermined level of precision or reliability. Each of these test termination criteria is set in advance by the examiner, preferably based on factors such as practicality and usefulness. Experience demonstrates that it is practical and useful to terminate testing after five minutes or 40 items, whichever occurs first in the testing session, or after a reliability of 0.90 has been attained. At the conclusion of the assessment procedure, the test data are stored and optional reports output.

The resultant test scores can be converted into hearing thresholds, which then can be used to screen test takers for hearing loss and other purposes. The equations that permit the forecast of hearing thresholds across the frequency range 0.5 through 8 kHz can be applied across other persons and testing occasions. However, the equations are specific to the test being administered. Thus, the equations are valid within the parameters of the test being administered and calibrated accordingly. Each speech recognition test developed in accordance with the present invention provides internally generated equations that permit the forecast of hearing thresholds. Hearing thresholds constitute the basic data used to construct an audiogram which is, itself, the primary data used to screen test takers for hearing loss and program hearing aids.

The hearing thresholds predicted from this test essentially yield a pseudo audiogram, again the primary data used to screen test takers for hearing loss and program hearing aids with proprietary software. The adaptive speech recognition testing procedure of the present invention is able to provide hearing threshold data which has up to now only been provided in clinical settings using pure-tone testing methodology. This testing procedure bypasses the clinic, making individualized hearing assessment possible in other settings via the internet.

A suitable adaptive speech recognition test in accordance with the present invention includes a computer-interactive assessment system developed at the National Technical Institute for the Deaf (NTID) known as the NTID Speech Recognition Test (NSRT®). The NSRT® is a diagnostic tool which produces data that when applied to the methods of the present invention can be used for hearing screening and programming hearing aids.

NSRT® is a computerized adaptive speech recognition test administered by a software application which uses naturalistic sentence-length utterances to efficiently provide meaningful information about the perceptual capabilities of listeners across a wide range of hearing thresholds, including mild to profound hearing losses. The NSRT® can be presented in two conditions: quiet and multi-talker babble background noise presented at +5 dB SNR. The stimuli are presented to respondents monaurally over earphones or binaurally in a sound field. The stimuli also may be presented in a sound field to one ear (monaurally) by isolating the non-test ear with an earplug. Test items are presented to respondents using a paired comparison discrimination task.

A common-item test was administered to a sample of respondents The relative difficulties ($d_i$ values) of the items in the item pool were computed by subjecting to Rasch scaling analysis the data obtained from administration of the common-item tests as described above. The responses of persons to the individual items constituted the raw data from which the item calibrations ($d_i$) and person measures ($b_v$) were obtained. In the scaling analysis, the raw data were organized in matrix form with persons appearing as rows and items appearing as columns. The data entries were 1's and 0's, where '1' represents a correct response of an individual to an item, '0' represents an incorrect response. Person scores are initially obtained by summing the 1's and 0's across items for each person tested. Item scores are initially obtained by summing the 1's and 0's across persons for each item in the test. These marginal sums are sufficient for estimating the $d_i$ and $b_v$ statistics. A calibrated item pool composed of approximately 600 items with associated $d_i$ values was developed in this way.

In addition to the item response data described above, other data were obtained for the individuals. These additional data included respondents' age and pure tone thresholds across the octave frequencies from 0.25 through 8 kHz. Respondents also were asked whether they perceived their hearing to be impaired. All of these data (i.e., NSRT® scores, pure tone thresholds, age and self-perception of hearing impairment/handicap) were used to study the empirical validity of the NSRT®, and a subset of the data (i.e., NSRT® scores, age and self-perception of hearing impairment/handicap) were used in accordance with the present invention to develop the algorithms for converting NSRT® scores to hearing thresholds at specific frequencies.

A calibrated item pool was created. Individuals were then tested with an adaptive NSRT®, substantially shorter than the common-item test, obtaining scores statistically equivalent to those obtained using the lengthier common-item test.

Using the scores, OLS regression analyses were conducted in accordance with the present invention to determine how well a weighted combination of the NSRT®, age and perceived hearing handicap/impairment variables (i.e., the formula below) predicted hearing thresholds across the frequency range 0.5 through 8 kHz by comparing pure tone testing results of each individual to the NSRT® predicted hearing thresholds. Note that, in the linear equations that resulted from these analyses, the NSRT® score was an average score from administrations of the test under quiet and +5 dB SNR background noise listening conditions. Furthermore, the NSRT® average score was itself transformed from logits (output from the Rasch scaling analysis) to a new metric ranging from 0 to 100. The correspondence between the logit metric and the new metric is perfect.

The equations presented below that permit forecasting of hearing thresholds across the frequency range 0.5 through 8 kHz can be applied across other persons and testing occasions. However, these equations are specific to NSRT® test performance.

The hearing threshold results calculated in accordance with the present invention from the NSRT® test scores yield a pseudo audiogram. Hearing thresholds provide the primary data used to screen for hearing loss and program hearing aids with proprietary software. The NSRT® testing procedure combined with the equations of the present invention are able to provide hearing threshold data which has up to now only been provided using pure-tone testing methodology. Our testing procedure bypasses the clinic, making individualized hearing assessment possible in other settings via the internet.

The NSRT® is composed of sentence-length utterances containing phonetic contrasts, primarily minimal pairs. Respondents must decide if the two sentences comprising each trial are the same or different from each other. The test includes items containing segmental contrasts in phonetic features of place, manner and voicing, as well as contrasts in vowels and sentence prosody (i.e., gross time-intensity variations in the speech waveform envelope combined with contrasts at the syllable and word levels). The NSRT® contains linguistic contrasts distributed over four broad phonetic categories: 1) sentence prosody; 2) voicing and vowels; 3) manner of articulation; and 4) place of articulation.

Contrasts in place of articulation are manifested within voiced and voiceless stop and fricative consonants (i.e., /p-t/, /p-k/, /t-k/, /b-d/, /b-g/, /d-g/, /f-s/, /f-ʃ/, /s-ʃ/, /θ-s/, /θ-ʃ/, /θ-f/, /z-v/, /v-ð/ and /z-ð/). The location of place contrasts varies in serial position within words and within sentences (i.e., word- and sentence-initial, medial and final positions; sentence-initial position is defined herein as the first phrase in a sentence; sentence-final position is defined as the last phrase in a sentence; and sentence-medial position is defined as all other locations within the sentence). Approximately 35% of all contrasts occurred in the place category. Examples of place contrasts are included in Table 1.

Contrasts in manner of articulation are manifested within voiced and voiceless stop and fricative consonants produced at the labial and alveolar places of articulation (i.e., /t-s/, /t-ʃ/, /t-θ/, /z-d/, /f-p/, /v-b/, and/d-ð/). The location of manner contrasts varies in serial position within words and within sentences (i.e., word- and sentence-initial, medial and final positions). Approximately 25% of all contrasts occurred in the manner category. Examples of manner contrasts are included in Table 1.

Contrasts in voicing are manifested within voiced-voiceless cognates (i.e., stops and fricatives), and contrasts in vowels are manifested across the features of tongue height and tongue advancement, as well as tense-lax vowel pairs. Again, the location of these contrasts varies in serial position within words and within sentences (i.e., word- and sentence-initial, medial and final positions). Approximately 20% of all contrasts occurred in the voicing and vowels category. Examples of voicing and vowel contrasts are included in Table 1.

Contrasts in sentence prosody (i.e., gross time-intensity variations in the speech waveform envelope combined with contrasts at the syllable and word levels) are manifested within and between phonological phrases, and their location varies within sentences. Approximately 20% of all contrasts occurred in the sentence prosody category. Examples of contrasts in sentence prosody are included in Table 1.

About 30% of the contrasts located within words occur in word-initial position; about 30% occur in word-final position; and about 40% occur in word-medial position. With regard to the location of contrasts within sentences, approximately 20% of contrasts occurred in sentence-initial position; about 30% occurred in sentence-final position; and about 50% occurred in sentence-medial position.

A fifth category of items representing repetitions of the standard sentence was also included in the item pool. This category did not contain any contrastive linguistic elements. Both comparison sentences are repetitions of the standard sentence and, as such, the correct response to each trial for items in this category is the 'Same.' About 10% of the item pool is composed of items in the 'Same' category.

The stimuli were digitally recorded at a sampling rate of 11.025 kHz and edited using commercially available signal processing software. Multiple renditions/tokens of each utterance were recorded, and a good quality, representative token was selected for inclusion in the test. The level of each utterance was adjusted to equalize the overall RMS voltage across stimuli in order to present each stimulus at an approximately equivalent overall level. Although the overall level of each sentence is equivalent, the RMS voltage within sentences varies with oscillations in the amplitude of the waveform.

As described above, the NSRT® uses a paired comparison discrimination task in which a standard sentence is paired with two comparison sentences. The presentation of an item begins with the presentation of a written representation of the standard sentence on a computer monitor. Approximately 1.5 seconds after the written sentence is displayed on the monitor and with it still remaining on the monitor, a spoken utterance (i.e., the first comparison sentence) is presented. The respondent must indicate if the comparison sentence is the same or different from the standard sentence. If the response is correct, then a second comparison sentence is presented while the printed version of the standard sentence remains displayed on the monitor. If the response is incorrect, then the next standard sentence (i.e., the next item) is presented. An item is scored correct if and only if the participant responds correctly to both comparison sentences. No partial credit is awarded. Therefore, if the response to the first trial is incorrect, the item is scored incorrect, and the standard sentence for the next item is presented. All responses were recorded on a computer hard drive.

Respondents are instructed to compare the standard and comparison sentences and indicate if the two sentences match (i.e., if the sentences have the same meaning). They are informed that any combination of 'Same' and 'Different' trials is possible, allowing for four potential response outcomes: S-D, D-S, D-D, and S-S. The test session begins after respondents demonstrate that they understand the task by successfully completing a set of 10 practice items. Examinees indicate whether the sentences presented in each trial are the 'same' or 'different,' by pressing a button on a response box, clicking a computer mouse or pressing a touch screen.

The NSRT® speech recognition testing experience is individualized, with items being selected "on the fly" from a large pool by an objective "up-down" method on the basis of the item information value. The items administered to each person are selected from a narrow range of difficulty spanning an individual's level of ability, which is itself constantly updated as items were administered during the testing process. The plurality of test items comprising the item pool includes about 600 unique sentence pairs.

Scores on the NSRT® have been shown to be highly reliable, having an internal consistency reliability of 0.98, as determined by the person separation reliability index commonly used in Rasch scaling analysis. Prespecification of the level of measurement accuracy or reliability required of respondents is built into the functionality of the adaptive testing software. As more test items are administered to a respondent, the accuracy (reliability) of the test score increases and so does the test administration time. Therefore, in practice, examiners need to determine an appropriate and desirable balance between the accuracy of test results and test administration time.

The NSRT® was administered in both quiet and background noise of 20-talker babble presented at +5 dB SNR. The adaptive test length, defined in terms of the number of items was set at 40 items and the time of test duration was set at 5 minutes. NSRT® uses 0.90 as the default setting for reliability and ±1.5 as the default setting for standard error.

The NSRT® operates using a pre-calibrated item pool in a system with three main components: (1) an item selection routine; (2) an ability estimation technique; and (3) one or more rules for test termination. The NSRT® can be self-administered on a home computer or wireless device, in a kiosk setting or in a clinical environment. A written representation of each standard sentence appears on a screen as comparison stimuli are presented acoustically. Examinees indicate whether the comparison sentences are the 'same' or 'different' via computer mouse or touch screen. If no response is produced within a preset response interval, the trial is scored incorrect. Items are scored correct if and only if both discrimination judgments (i.e., both trials) are correct. Testing begins with several practice items.

NSRT® differs from conventional speech recognition tests in that the testing experience is individualized and automated, with items being selected by an objective "up-down" method on the basis of their information value. The items are scaled along a continuum extending from low to high degrees of speech recognition difficulty, and the continuum of item difficulty generally reflects the listener's ability to perceive acoustic and phonetic properties of speech, such as phonetic features of place, manner and voicing. Since the test is administered by a software application, it may be delivered over the internet and/or self-administered by test takers. Importantly, the adaptive item selection procedure enhances measurement precision for individuals in comparison to conventional word recognition tests because of the systematic manner in which the up-down psychophysical method brackets the respondent's speech recognition ability level within progressively smaller ranges of measurement error. The standard error ($s_e$) determines the step size for the up-down procedure, and the NSRT® uses a setting of ±1.5 $s_e$ as the default value.

FIG. 1 illustrates a flowchart of the operation of the NSRT® adaptive testing system. The application uses pre-existing data to determine the difficulty ($d_i$) of the first test item to be administered to an examinee to enhance the efficiency and accuracy of measurement. Specifically, the first item is empirically related to one or more of the following three variables: (1) prior performance on the NSRT®; (2) the respondent's age expressed in years; and (3) an indicator variable reflecting a respondent's perception of whether they suffer from a hearing impairment/handicap. Using equations derived from OLS regression techniques, these data are used to guide the NSRT® application where testing is to begin.

The NSRT® test procedure is composed of two stages. The first stage of NSRT® testing, the routing test, proceeds until an examinee responds correctly and incorrectly to the items presented. To illustrate, the first item administered has, for example, $d_i$=0.25 logit. If the examinee responds correctly (incorrectly), an item of greater (lesser) difficulty is administered next. The increment (decrement), here 0.50 logit, remains fixed and constant at this stage of testing. Thus, the second item to be administered will be that item in the pool having difficulty closest to +0.75 or −0.75 logit depending on the response to the previous item. The fixed increment (decrement) is continued until at least one correct and one incorrect response have been observed.

It will be the case that some individuals tested may be outside the ability limits to which the NSRT® is sensitive. Thus, for individuals for whom both correct and incorrect responses have not been observed upon reaching the extremities of difficulty or easiness, NSRT® testing terminates with a message indicating that these individuals have speech recognition ability levels which are indeterminate. The maximum length of the routing test (M) was set at M=10 items at the onset of testing.

When at least one correct and one incorrect response to the NSRT® items have been observed for an individual, a finite maximum likelihood estimate of ability ($b_v$), as well as its associated standard error $s_e$, is computed. This occurs in the second stage of testing. The numerical estimation method employed here possesses the property that an individual's number right or raw score is a sufficient statistic for estimation of the ability parameter.

Using the estimate of ability $b_v$ computed in the previous programming step, test items in the NSRT® pool that have not already been administered are evaluated for their potential to provide additional information about the examinee. Specifically, the next item to be administered will be that item which has $d_i$ closest to $b_v$, with the further condition that the difference between the ability estimate and the selected item's difficulty must be less than the standard error associated with the ability estimate. Otherwise, testing is terminated with a message that NSRT® items of appropriate difficulty have been exhausted.

After each newly selected test item is presented and the examinee's response is evaluated for correctness/incorrectness, the $b_v$ is revised, making use of the additional information. The revised $b_v$ is compared, as earlier, with the $d_i$ of items remaining in the pool that have not already been administered. In this way, NSRT® items continue to be administered to an examinee as long as the difference between the item difficulty and each newly computed $b_v$ remains within a decreasing standard error of measurement.

Testing is terminated when: (1) items remaining in the pool are of inappropriate difficulty; (2) an individual has responded to L items; (3) the testing session reaches a predetermined time limit; or (4) an individual has been tested to a predetermined level of precision or reliability. Each of these test termination criteria is set in advance by the examiner. For the NSRT®, testing is terminated after five minutes or 40 items, whichever occurs first in the testing session, or after a reliability of 0.90 has been attained. At the conclusion of the assessment procedure, the NSRT® test data are stored and optional reports output.

Test score data obtained from earlier versions of the NSRT® (Bochner, J., Garrison, W., Sussman, J. and Burkard, R. (2003), "Development of materials for the clinical assessment of speech recognition: The Speech Sound Pattern Discrimination Test," Journal of Speech, Language and Hearing Research, 46, 889-900; Doherty, K., Bochner, J., Garrison, W., Richards, G., Holstad, K. and Sims, D., "An Adaptive Test for the Clinical Measurement of Speech Recognition," Poster presented at Audiology NOW!, Boston, Mass., Mar. 30, 2012) have been used in accordance with the present invention to establish the statistical association between hearing thresholds at specific frequencies and speech recognition ability. Specifically, data obtained in the 2003 study found that performance on the NSRT® could be modeled in terms of a linear combination of four predictor variables that included high frequency pure tone average, speech reception/recognition threshold or SRT (a measure used by audiologists to corroborate pure tone average at frequencies 0.5, 1 and 2 kHz), age, and a self-report indicator variable reflecting respondents' perception whether they suffered from hearing impairment/handicap. A different representation of the earlier model enables the determination of hearing thresholds at specific frequencies in dB HL (the octave frequencies from 0.5 to 8 kHz) using NSRT® performance, age, and the self-report hearing handicap variable as predictor variables as described below.

The following documents are each hereby incorporated by reference in their entirety: Bochner, J., Garrison, W. and Palmer, L. (1986), "A closed-set sentence protocol for assessing speech discrimination in deaf individuals: The Speech Sound Pattern Discrimination Test," *Ear and Hearing*, 7(6), 370-376; Bochner, J., Garrison, W., and Palmer, L. (1992), "Simple discrimination isn't really simple: A confirmatory analysis of the Speech Sound Pattern Discrimination Test," *Scandinavian Audiology*, 21(1), 37-49; Bochner, J., Garrison W., Palmer, L., MacKenzie, D., and Braveman, A. (1997), "A computerized adaptive testing system for speech discrimination measurement: The Speech Sound Pattern Discrimination Test (SSPDT)," *Journal of the Acoustical Society of America*, 101(4), 2289-2298; Bochner, J., Garrison, W., Sussman, J. and Burkard, R. (2003), "Development of materials for the clinical assessment of speech recognition: The Speech Sound Pattern Discrimination Test," *Journal of Speech, Language and Hearing Research*. 46, 889-900; Bochner, J. H., Garrison, W. M. and Doherty, K. A. (2015), "The NTID Speech Recognition Test: NSRT," *International Journal of Audiology*; Garrison, W. M. and Bochner, J. H. (2015), "Applications of the NTID Speech Recognition Test (NSRT)," *International Journal of Audiology*; and Doherty, K., Bochner, J., Garrison, W., Richards, G., Holstad, K. and Sims, D., "An Adaptive Test for the Clinical Measurement of Speech Recognition," Poster presented at Audiology NOW!, Boston, Mass., Mar. 30, 2012.

The results of regression analyses applied according to the present invention, using earlier test score data, are summarized in the chart below. Predictor variables were NSRT® score, respondent age and perception of hearing handicap. Importantly, in the 2003 study, hearing thresholds averaged across 2, 4 and 8 kHz (high frequency pure tone average) and the speech reception threshold (SRT) were used to predict speech recognition (NSRT) scores. In the present work, however, neither an average of hearing thresholds nor SRT are involved. The present work addresses the prediction of hearing thresholds at specific frequencies and, as such, differs substantially from previously disclosed information. In particular, the mathematical relationship among NSRT scores, hearing thresholds, respondent age and self-report of hearing handicap disclosed in the present work is completely different from the relationship described in 2003 because the present work does not make use of average hearing thresholds or SRT in any way. Reported in the chart below are the unstandardized coefficients or weights for each of the three predictor variables, the multiple R, and $R^2$, the proportion of total variance in hearing threshold accounted for by linear combinations of the independent variables.

In the chart below, a series of regression equations can be formed from the values shown in columns 2-5. To illustrate, the last row shown in the chart (corresponding to the average dB hearing loss at thresholds 2, 4, and 8 kHz), generally expressed as high frequency hearing loss for pure tones, is generated from the following equation:

dB loss=139.47−1.80(NSRT®)+0.09(Age)+10.69 (Status)

where NSRT®=the average of NSRT® measures obtained under two listening conditions;
Age=chronological age expressed in years; and
Status=a value of 1 or 0 reflecting an individual's report of the presence/absence of hearing handicap.

Regression Analysis Summary

Similar equations, using the weights shown in the chart above, can be formed in accordance with the present invention to predict hearing thresholds at specific frequencies (i.e., 0.5 to 8 kHz). The results of these computations can then be combined to construct a pseudo audiogram for an individual based upon NSRT® performance.

The general form of the equation used to compute hearing thresholds across the frequencies 0.5 to 8 kHz is as follows:

$$y_j = b_{j0} + b_{j1}x_1 + b_{j2}x_2 + b_{j3}x_3, j=1-5\{\text{frequencies}\}$$

where:
$x_1$=average of NSRT® measures obtained under the quiet and +5 dB SNR background noise listening conditions;
$x_2$=chronological age expressed in years; and
$x_3$=self-report of perceived hearing handicap/impairment (yes=1, no=0).

The metric for $x_1$ in the equation above ranges from 0 to 100 and is itself a transformation of the logit metric used in Rasch scaling analysis. The data value for $x_1$ is an average of the NSRT® measures obtained in the quiet and +5 dB SNR background noise listening conditions, expressed on the 0 to 100 scale. There are five (j=5) sets of constants ($b_{j0}$, $b_{j1}$, $b_{j2}$, $b_{j3}$), corresponding to the five frequencies (0.5, 1, 2, 4, and 8 kHz) for which individuals' hearing thresholds are computed.

Example 1

To illustrate the application of the above NSRT® test using the above equation, which was subsequently developed in accordance with the present invention, NSRT® test results of a male respondent aged 66 years who, perceived that he suffered from a mild to moderate hearing loss will be utilized. The test items were presented to this respondent binaurally in a sound field. The respondent attained an NSRT® score=64 in quiet, and a score=50 in background noise. The average of scores in the two conditions is 57. In the equation above, $x_1$=57 (NSRT® average score), $x_2$=66 (age in years), and $x_3$=1 (perceived hearing handicap, yes=1).

Values of the $b_{j0}$, $b_{j1}$, $b_{j2}$, and $b_{j3}$ constants for the computation of the respondent's hearing threshold at 0.5 kHz are {103.69, −1.23, −0.21, 7.55}, respectively. When these constants are applied to the algorithm for computing hearing threshold, dB HL at 0.5 kHz is calculated as follows:

$$\text{dB loss} = 103.69 - (1.23 * 57) - (.21 * 66) + (7.55 * 1)$$
$$= 27.27$$
$$= 30 \text{ (rounded to the nearest multiple of 5)}$$

At 1 kHz, $b_{j0}$, $b_{j1}$, $b_{j2}$, and $b_{j3}$ constants are {133.27, −1.59, −0.30, 9.40}, respectively.

| Dependent Variable | $B_1$ (NSRT ®)[a] | $B_2$ (Age)[b] | $B_3$ (Status)[c] | Constant | Multiple R | $R^2$ |
|---|---|---|---|---|---|---|
| Threshold (500 Hz) | −1.23 | −.21 | 7.55 | 103.69 | .72 | .52 |
| Threshold (1000 Hz) | −1.59 | −.30 | 9.40 | 133.27 | .81 | .65 |
| Threshold (2000 Hz) | −1.92 | −.17 | 7.51 | 154.00 | .86 | .74 |
| Threshold (4000 Hz) | −1.84 | .06 | 11.10 | 144.57 | .88 | .77 |
| Threshold (8000 Hz) | −1.67 | .38 | 13.57 | 122.91 | .86 | .74 |
| PTA (.5, 1, 2 kHz) | −1.58 | −.23 | 8.15 | 130.32 | .84 | .71 |
| Average (1, 2, 4 kHz) | −1.78 | −.14 | 9.33 | 143.95 | .90 | .81 |
| Average (2, 4, 8 kHz) | −1.80 | .09 | 10.69 | 139.47 | .90 | .81 |

[a] NSRT ® metric ranges 0-100 and is a transformation of the Rasch ability scale typically expressed in logits. In these analyses, NSRT ® is an average of measures obtained in quiet and +5 dB SNR listening conditions.
[b] Age is expressed in years
[c] Perceived hearing impairment (Yes = 1, No = 0)

At 2 kHz, $b_{j0}$, $b_{j1}$, $b_{j2}$, and $b_{j3}$ constants are {154.00, −1.92, −0.17, 7.51}, respectively.

At 4 kHz, $b_{j0}$, $b_{j1}$, $b_{j2}$, and $b_{j3}$ constants are {144.57, −1.84, 0.06, 11.10}, respectively.

At 8 kHz, $b_{j0}$, $b_{j1}$, $b_{j2}$, and $b_{j3}$ constants are {122.91, −1.67, 0.38, 13.57}, respectively.

In this example, $x_1=57$, $x_2=66$, and $x_3=1$ in all calculations of hearing threshold across the frequencies 0.5 to 8 kHz. Results of all calculations are rounded to the nearest multiple of 5 dB, consistent with the incremental steps normally observed in pure tone assessment with clinical audiometers. For the respondent whose data were employed in this example, hearing thresholds across the frequencies 0.5, 1, 2, 4, and 8 kHz were calculated to be 30, 30, 40, 55, and 65 dB HL, respectively. These dB HL data can be used to screen test takers for hearing loss or to serve as input for proprietary software used to program and fit hearing aids.

Example 2

To elucidate the relationship between NSRT® and hearing thresholds developed in accordance with the present invention further, the data can be divided into subsamples based upon PTA results. Here, normal hearing sensitivity was defined as PTA less than or equal to 20 dB HL. Average hearing losses falling in the 21-40 dB HL range were considered mild, while those falling in the range 41-55 dB HL were considered moderate. Average hearing losses in the 56-70 dB HL range were considered moderately severe.

Figure 2:
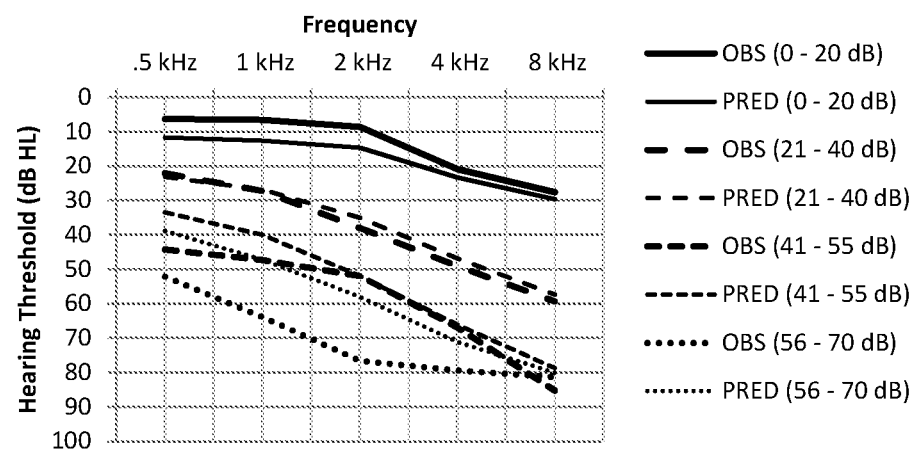
FIG. 2 provides an illustration of the relationship between the NSRT® and hearing thresholds depicting observed vs. predicted hearing thresholds for four subgroups of respondents.

For each of the four subsamples of data, hearing thresholds for the frequencies from 0.5 to 8 kHz were computed and compared with those predicted from the regression models. The accuracy of observed (OBS) and predicted (PRED) results is shown graphically in FIG. 2.

In sum, as the example shows, the NSRT® test result reasonably determines hearing thresholds in accordance with the present invention for individuals with mild to moderate hearing losses. Specifically, NSRT® scores are entered into a regression model to determine hearing thresholds for persons having mild to moderate hearing loss with 95% accuracy (i.e., statistical equivalence) between predicted hearing thresholds and those obtained in the clinical setting across the octave frequencies 0.5 to 8 kHz. Accuracy falls off as hearing losses approach the severe end of the spectrum. The predicted thresholds then can be used to screen test takers for hearing loss and as input to software applications designed to program hearing aids.

This capability would be very useful for companies selling amplification devices to consumers directly over the internet because it would enable customers to self-administer a hearing test (i.e., the NSRT®) in their homes via the internet or at kiosks located in pharmacies and other places, with the test results being used to screen test takers for hearing loss and/or to program the amplification device to fit the characteristics of their hearing loss.

What is claimed is:

1. A method for determining hearing thresholds of an individual in the absence of pure-tone testing, comprising:
    developing a pool of items comprising a plurality of items, each item comprising two trials and each trial comprising a paired comparison of utterances, wherein the utterances can be the same or different from one another and a difference comprises acoustic and phonetic features occurring within minimal pairs;
    administering each item from the plurality of items to a first group of individuals having hearing loss to obtain a response to each of the items;
    subjecting the responses to a scaling analysis to assign a difficulty value ($d_i$) and an associated standard error ($s_e$) to each of the items to create a calibrated item pool comprising items scaled along a continuum of speech recognition ability;
    administering an adaptive speech recognition test comprising items from the calibrated item pool to an individual having hearing loss to obtain a response to the calibrated items based upon the individual's speech recognition ability;
    calculating a test score for the individual based upon the responses to the calibrated items; and
    applying multiple regression statistical methods to the test score of the individual together with variables comprising the individual's age and perception of hearing handicap to develop an equation converting the individual's adaptive speech recognition test score to hearing threshold values at several frequencies.

2. The method of claim 1, further comprising screening for hearing loss or programing an amplification device using the individual's hearing thresholds in a test ear if the stimuli are presented to one ear only or in a better ear if the stimuli are presented simultaneously to both ears.

3. The method of claim 1, wherein administering the adaptive speech recognition test comprises administering the test across one or more listening conditions comprising quiet and background noise listening conditions.

4. The method of claim 3, wherein the calculated test score is obtained by averaging a score obtained under the quiet listening conditions and a score obtained under the background noise listening conditions.

5. The method of claim 1, wherein the test items are composed of sentence-length utterances which include linguistic contrasts in four phonetic categories.

6. The method of claim 5, wherein the utterances are digitally recorded and edited to develop a set of audio files and each audio file is composed of one sentence-length utterance.

7. The method of claim 1, wherein the adaptive speech recognition test comprises a paired comparison discrimination task in which each item composed of a standard sentence is paired with two comparison sentence trials, wherein in the first trial a written representation of the item's standard sentence is presented and while the written sentence is displayed, a spoken utterance of the first comparison sentence for the first trial is presented; the individual then indicates if the first comparison sentence is the same or different from the standard sentence; if the response to the first trial is correct, then a subsequent spoken utterance comprising the second trial comparison sentence is presented while the same standard sentence is displayed; the individual then indicates if the second comparison sentence is the same or different from the standard sentence; and an item is scored correct if the individual responds correctly to both comparison sentence trials.

8. The method of claim 7, wherein a new standard sentence is presented when the response to the first trial comparison sentence is incorrect or after the response to the second trial; and a new item is selected from the plurality of items comprising the item pool based on responses to previously presented items using an up-down method of item selection.

9. The method of claim 1, wherein the adaptive speech recognition test initially proceeds until the individual correctly responds to one item and incorrectly to another of the items presented; if the individual responds correctly, an item of greater difficulty is administered next, if the individual responds incorrectly, an item of lesser difficulty is administered next; an increment or decrement remains fixed and constant a second item to be administered will be an item in the plurality of items comprising the item pool having a difficulty closest to an adjacent logit; and the fixed increment or decrement is continued until at least one correct and one incorrect response has been observed.

10. The method of claim 1, wherein administering items of the adaptive speech recognition test to the individual when at least one correct and one incorrect response to the items has been observed, a finite maximum likelihood estimate of ability ($b_v$), as well as associated standard error ($s_e$), is computed; using the computed estimate of ability ($b_v$), items that have not already been administered which have ($d_i$) closest to ($b_v$) are administered, wherein a difference between the ability estimate and a selected item's difficulty is less than the standard error associated with the ability estimate; otherwise, testing is terminated with a message that items of appropriate difficulty have been exhausted.

11. The method of claim 10, wherein after each newly selected test item is presented and the individual's response is evaluated for correctness/incorrectness, the ($b_v$) is revised, making use of additional information; the revised ($b_v$) is compared with the ($d_i$) of items remaining that have not already been administered wherein items continue to be administered to the individual as long as a difference between the continued item difficulty and each newly computed revised ($b_v$) remains within a decreasing standard error of measurement.

12. The method of claim 1, wherein testing is terminated when: (1) remaining items are of inappropriate difficulty; (2) the individual has responded to the items in the test session; (3) a testing session reaches a time limit; or (4) the individual has been tested to a predetermined level of precision or reliability.

13. The method of claim 10, wherein item difficulty ($d_i$) and person ability ($b_v$) estimates are on a same numerical scale, facilitating a selection of items of appropriate difficulty to estimate the individual's ability level and the associated standard error following the administration of each test item.

14. The method of claim 1, wherein the acoustic and phonetic features comprise four categories of linguistic contrasts which comprise:

contrasts in place of articulation manifested within voiced and voiceless stop and fricative consonants comprising /p-t/, /p-k/, /t-k/, /b-d/, /b-g/, /d-g/, /f-s/, /f-ʃ/, /s-ʃ/, /θ-s/, /θ-ʃ/, /θ-f/, /z-v/, /v-ð/ and /z-ð/, the location of place contrasts varies in serial position within words and within sentences comprising word- and sentence-initial, medial and final positions; wherein sentence-initial position is the first phrase in a sentence; sentence-final position is the last phrase in a sentence; and sentence-medial position is all other locations within the sentence;

contrasts in manner of articulation are manifested within voiced and voiceless stop and fricative consonants produced at the labial and alveolar places of articulation comprising /t-s/, /t-ʃ/, /t-θ/, /z-d/, /f-p/, /v-b/, and /d-ð/, the location of manner contrasts varies in serial position within words and within sentences comprising word- and sentence-initial, medial and final positions;

contrasts in voicing are manifested within voiced-voiceless cognates comprising stops and fricatives, and contrasts in vowels are manifested across the features of tongue height and tongue advancement, as well as tense-lax vowel pairs, wherein the location of the contrasts in voicing and in vowels varies in serial position within words and within sentences comprising word- and sentence-initial, medial and final positions; and contrasts in sentence prosody, comprising gross time-intensity variations in the speech waveform envelope combined with contrasts at the syllable and word levels, are manifested within phonological phrases, and the location of the contrasts in sentence prosody and at the syllable and word levels varies within sentences.

15. The method of claim 1, wherein the developed equation comprises:

$y_j = b_{j0} + b_{j1}x_1 + b_{j2}x_2 + b_{j3}x_3$ where:

j = 1-5 {frequencies};

$b_{j0}$ = value of regression intercept;

$b_{j1}$ = regression coefficient for $x_1$;

$b_{j2}$ = regression coefficient for $x_2$;

$b_{j3}$ = regression coefficient for $x_3$;

$y_i$ = hearing threshold;

$x_1$ = test measures obtained under quiet, noise or the average of both listening conditions;

$x_2$ = chronological age expressed in years; and $x_3$ = self-report of perceived hearing ability.

* * * * *